United States Patent
Quintana

(10) Patent No.: US 11,714,297 B2
(45) Date of Patent: Aug. 1, 2023

(54) CORRECTIVE LENS APPARATUS AND METHOD

(71) Applicant: Alejandro A. Goebel Quintana, Houston, TX (US)

(72) Inventor: Alejandro A. Goebel Quintana, Houston, TX (US)

(*) Notice: Subject to any disclaimer, the term of this patent is extended or adjusted under 35 U.S.C. 154(b) by 392 days.

(21) Appl. No.: 16/853,259

(22) Filed: Apr. 20, 2020

(65) Prior Publication Data

US 2020/0249497 A1 Aug. 6, 2020

Related U.S. Application Data

(63) Continuation of application No. 15/754,506, filed as application No. PCT/US2016/049110 on Aug. 26, 2016, now Pat. No. 10,627,648.

(60) Provisional application No. 62/210,024, filed on Aug. 26, 2015.

(51) Int. Cl.
| | |
|---|---|
| *G02C 7/02* | (2006.01) |
| *G02C 1/00* | (2006.01) |
| *G02C 7/08* | (2006.01) |
| *G02C 1/06* | (2006.01) |
| *G02C 7/16* | (2006.01) |
| *A61F 9/02* | (2006.01) |

(52) U.S. Cl.
CPC .............. *G02C 7/02* (2013.01); *G02C 1/00* (2013.01); *G02C 1/06* (2013.01); *G02C 7/086* (2013.01); *G02C 7/16* (2013.01); *A61F 2009/021* (2013.01)

(58) Field of Classification Search
CPC .......... G02C 7/08; G02C 7/086; G02C 7/088; G02C 7/02; G02C 7/16; G02C 1/00; G02C 1/06; A61F 2009/021; A61F 9/02; A61B 33/002
USPC ..................... 351/159.7, 158, 83; 2/431, 439
See application file for complete search history.

(56) References Cited

U.S. PATENT DOCUMENTS

| | | | | |
|---|---|---|---|---|
| 10,627,648 B2* | 4/2020 | Quintana | ................. | G02C 7/02 |
| 2004/0165144 A1* | 8/2004 | Nishikata | ................. | G02C 7/16 |
| | | | | 351/159.57 |
| 2005/0193479 A1* | 9/2005 | Atta | ..................... | A63B 33/004 |
| | | | | 2/440 |
| 2006/0073771 A1* | 4/2006 | mandler | ........... | B29D 11/00932 |
| | | | | 451/325 |
| 2013/0141693 A1* | 6/2013 | McCabe | ........... | B29C 45/14819 |
| | | | | 351/159.56 |
| 2016/0054582 A1* | 2/2016 | Rauter | ..................... | A42B 3/22 |
| | | | | 351/159.52 |
| 2017/0239528 A1* | 8/2017 | Barone | ................ | A63B 33/004 |

* cited by examiner

*Primary Examiner* — William R Alexander
(74) *Attorney, Agent, or Firm* — Donn K. Harms

(57) ABSTRACT

A unitary lens structure is provided which is employable with spectacles as well as goggles and safety eyewear. The lens is formed as a unitary structure with projections having surfaces which are machinable for prescription eyewear extending from a first side surface of a larger shield. Damage from cracking of the shield at the intersections with the projection perimeters is prevented by non linear connections between the two surfaces.

17 Claims, 9 Drawing Sheets

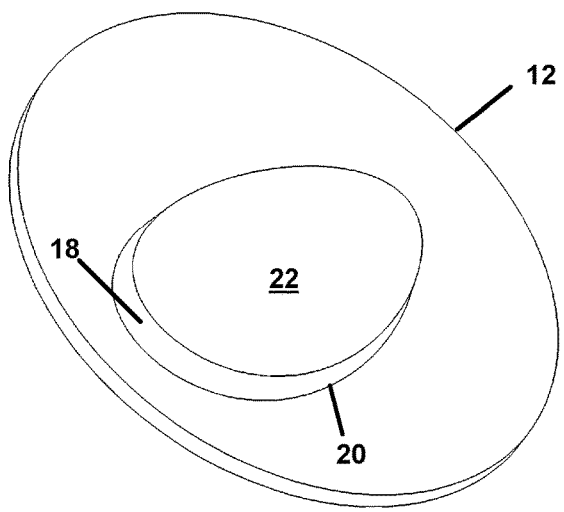
FIG. 12
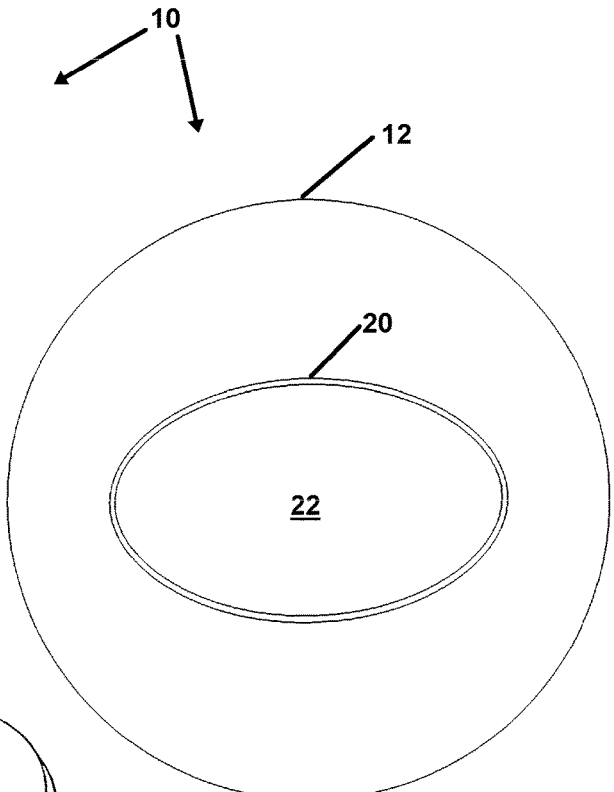
FIG. 13
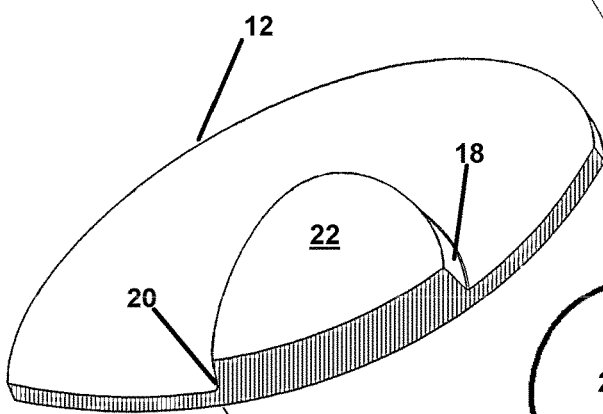
FIG. 14
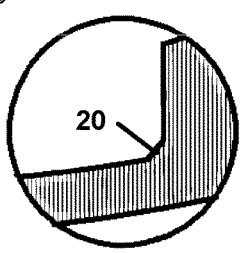
FIG. 15a
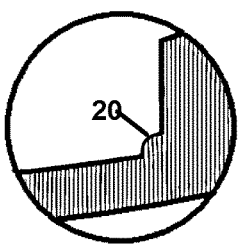
FIG. 15b
FIG. 15c
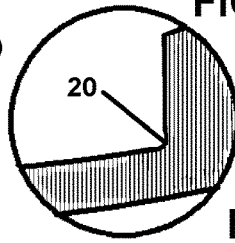
FIG. 15d

2

CORRECTIVE LENS APPARATUS AND METHOD

This application is a Continuation of U.S. patent application Ser. No. 15/754,506 filed on Feb. 22, 2018 which was a national filing of PCT/US16/49110 filed on Aug. 26, 2016, which claims priority to U.S. Provisional Patent Application Ser. No. 62/210,024 filed on Aug. 26, 2015, all of which are incorporated in their respective entirety by this reference thereto.

BACKGROUND OF THE INVENTION

1. Field of the Invention

The present invention relates generally to corrective lenses employed in eyewear such as eyeglasses, protective eyewear, and goggles. More particularly, the disclosed system and method relates to a lens having a first portion forming a shield or surrounding portion formed of optically correct material and having one or a plurality of projections permanently positioned thereon for formation of corrective lenses. So configured the device forms a unitary structure where the perimeter of the first portion of the lens is adapted for engagement in an eyewear frame or goggle or other lens frames.

2. Prior Art

Individuals with eyesight problems have turned to corrective eyewear for hundreds of years. As a general rule, such eyesight problems are a result of the physical characteristics of the eye of the person requiring corrective lenses. Over the duration such corrective lenses have been provided to users requiring them. The basic nature of grinding lenses to refocus the image captured by the eye of the user onto the receptive rear surface of their eye in a manner rendering clearer vision has progressed to provide corrections for issues other than near or far sightedness. However, the basic premise of positioning a lens in front of the eye of the user to refocus incoming light is still present today.

In some instances the nature of construction of corrective lenses, especially in combination with safety or protective eyewear, has been less than adequate. For example, users of corrective lenses who suffer from severe farsightedness require very thick lenses to correct their vision, which are not well adapted for use in combination with a shield type eyewear such as goggles. Further, such thick lenses have perimeters which limit the engagement to eyeglass frames.

Further, those with nearsightedness or farsightedness or who suffer from other vision acuity problems also have problems trying to wear protective goggles such as military members who wear goggles, or others who wear sport goggles for activities such as skiing or motorcycling. The problem of corrective lenses is also an issue when combined with workers who must wear safety goggles.

Conventionally, such users have been forced to try and fit their eyeglasses within the cavity of the goggle or safety goggle covering their eyes. In such a combination, the user must view their surroundings through both the goggle lens, and their own lenses positioned in-between the goggle lens and their face. Such has led to poor vison from fogging, glare from the interaction of spaced refraction surfaces, shadow images caused by the spaced lenses, and other issues caused by the interaction between the eyeglass lenses spaced from the goggle lens or lenses.

In prior art a partial solution to the problem has been advanced. For example U.S. Pat. No. 8,814,349 (Quintana), while a leap forward, in the concept of providing a unitary structure of corrective lenses and panoramic or shielding lens, could use improvement in the taught construction of the unitary structure. Quintana, while teaching the novel concept of using two projecting portions rising from one side of a first panoramic lens for formation of ophthalmic lenses, makes no accommodation for the risk of cracking along the perimeter of the projecting portions at their intersection with the front panoramic lens. Additionally, refraction of light through the sidewall of the projecting portions and adjacent their intersection with the front panoramic lens, as taught by the Quintana reference, may generate refractive qualities such as colorized light, which has been found to be distracting to users. Additionally, when employed for goggles which form a sealed cavity in front of the face of the user, the dissimilar thicknesses of the panoramic lens or shield areas thereof with projecting portions, can have thermal issues during formation due to the retention of heat in the thicker areas. Additionally, no prior art teaches a manner in which smaller projections on a curved panoramic shield can be ground to required characteristics to provide vision correction to a wearer.

As such, there exists an unmet need, for a corrective lens formable upon a surface of a thinner panoramic lens, where the intersection of the perimeter of the projecting material from which the ophthalmic lens is formed and the planar panoramic front lens is configured to prevent cracking and stress fractures over time and temperature differentials. Such a device should provide a form which is employable in single lenses of eyewear as well as in dual lens configurations of protective eyewear shields and sport and protective goggle devices and in shapes which allow for formation of progressive lenses in both the horizontal and vertical direction. Still further, such a device and method should provide projections on the frontal panoramic lens which are machinable to corrective lenses using conventional lens grinding machinery, in spite of the large and highly curved panoramic lens surrounding the projecting portions.

The forgoing examples of related art and limitations related therewith are intended to be illustrative and not exclusive, and they do not imply any limitations on the invention described and claimed herein. Various limitations of the related prior art will become apparent to those skilled in the art upon a reading and understanding of the specification below and the accompanying drawings.

OBJECTS OF THE INVENTION

It is an object of this invention to provide a unitary structure of a first curved or panoramic lens having one or a plurality of projecting portions formed thereon which may be cut to form ophthalmic lenses.

It is a further object of this invention to provide such a unitary structure where the first lens on which the projecting portion is formed, surrounds the projecting portion in a thinner cross section of optical material which may be fit to frames heretofore precluded for users with thick lens prescriptions.

It is a further object of this invention to eliminate or at least minimize the potential for cracking of the thinner front or panoramic lens at the intersection of the perimeter sidewalls of the projecting portions and the panoramic lens they are formed upon.

It is a further object of this invention to provide the projecting portions formed upon a surface of a larger curved lens to be machinable using conventional lens grinding machinery despite the large and curved first lens portions surrounding them.

It is also an object of this invention to provide the projecting portions formed to unitary structure with the surrounding panoramic first lens, in shapes which may be cut to allow for progressive lenses in both the horizontal and vertical directions.

These and other objects, features, and advantages of the present lens invention and system herein, as well as the advantages thereof over existing prior art, which will become apparent from the description to follow, are accomplished by the improvements described in this specification and hereinafter described in the following detailed description which fully discloses the invention, but should not be considered as placing limitations thereon.

SUMMARY OF THE INVENTION

The present invention is a lens formed into a unitary structure featuring a first lens portion formed in a generally concave panoramic shape and having a plurality of projecting portions on a rear surface, defined in shape by a perimeter edge, rising from a permanent connection with a first surface of the first lens portion. The cross sectional thickness of the first lens portion, which curves around and surrounds the projecting portions, is thinner than the cross sectional thickness of the area within the bounds of the perimeter of the projecting portions, rising from an inner or first side of the first lens portion.

In a preferred mode of the device, the radii of the first lens portion or shield can vary slightly to better accommodate the portion in a central area of the shield where the projections are located and reduce distortion further. For example, the first lens portion or shield can have a general radii of a front surface of the shield or first lens portion, which is 75 mm. However, the central area where the projections extend can be 65 mm (flatter). This slight flattening of the arc in the central portion has been found to increase the range of possible corrective prescriptions to be produced. However, the difference in radii would not be noticeable to the naked eye, and the first portion or shield will maintain, in general, its original shape for cosmetics and fitment to conventional frames and goggle housings.

This first lens portion is optically correct across its entire surface such that the thinner surrounding area, on both sides of the central portion, is optically correct and significantly thinner in cross section to allow engagement within an eyeglass frame or goggle but still adapted for an engagement to temple portions to form a shield.

In all modes of the device herein, the intersection of the perimeter edge of the sidewall defining the shape of the projecting portion employed for lens formation, with the first surface for the first lens portion, is preferably neither a perpendicular intersection of two planar surfaces nor an intersection of a straight line extending up the sidewall surface of the projecting portion.

In all modes of the device herein, that intersection of the sidewall of the perimeter of the projecting portions which defines a shape of the projecting portions, is preferably formed such that the line running up the sidewall surface from the intersection with the first surface of the first lens portion, is non linear in that a portion of the sidewall changes direction relative to the rest of the sidewall extending to the edge of the machinable surface of the projecting portion.

In all modes of the device herein, one or, more preferably, a plurality of such projecting portions, are engaged with the surrounding optically correct panoramic lens in a manner to yield a permanent connection between the two, which forms a unitary structure with minimal, if any, optical distortion therethrough. This connection between the projecting portion or portions is preferably achieved by molded formation of a unitary structure of the projecting portions and the first lens portion or shield defining a panoramic lens.

In forming a unitary structure, the projections and first lens portion or shield can be molding as a single unit, or the projections may be co-molded into the first lens portion. In co-molding, the projections are pre-formed and subsequently communicated into the mold for the first lens portion, wherein a first surface of the projections melts and joins to the projecting portions to form a unitary structure.

As noted, it is preferable that the intersection of the perimeter sidewall of the projections, and the central portion of the first lens portion, is not perpendicular. Thus, in molding or forming the unitary structure of the first lens portion and projections, this intersection is preferably formed curved or angled. It is also preferred that a width of the intersection of the angled or curved surface forming the connection be small and not rise more than a millimeter above the surface of the first lens portion, because experimentation has shown this to minimize any distortion or light refraction issues.

Additionally, if formed of a curved first lens portion or shield with a plurality of projecting portions thereon for engagement to goggles or an eyeglass frame, a polarizing layer may be placed in-between the material forming the first lens portion and the projecting portion which is machinable to form the corrective lens. This will provide polarized light transmission to the wearer. Such may be accomplished by layering the first lens portion.

Still further, the shape of the projecting portion defined by the sidewall intersecting the first surface of the first lens portion can be formed in shapes, as shown herein, or other shapes, which will allow for cutting of progressive lenses therein for the user. For example, one such shape, as shown in the figures, has a wider diameter adjacent the two ends of the curved first lens portion and narrows and extends toward the middle.

This preferred shape allows for portions of the projecting portion to extend closer to the bridge of the nose, while concurrently extending to the temple and well below the nose. This extended rectangular shape with a curve extending from a nose-side to the lower edge allows for formation of progressive lenses which are highly customized to a user where the progressive lens can be both horizontal from top to bottom and sideways from nose to temple. Since the surrounding section of the first lens portion is significantly thinner than the unitary portion of the projecting portion and first lens portion, the formed lens or shield can be configured for users.

Additionally shown is a preferred removable tooling engagement member which may be formed as part of the unitary lens. By formation of this tooling engagement member, in a break away or removable engagement extending perpendicular from the axis of the unitary lens and in a centered position, it allows for machining of the raised surfaces of the projecting portions to form corrective lenses by an engagement of the unitary structure to a lens machining apparatus using the removable projecting member. As noted, this tooling engagement, and the unitary structure of the first lens and projecting portion, overcomes the problems associated with the prior art, where the large curved panoramic first lens portion blocks engagement in a conventional fashion to lens grinding machines. Once the projecting portion surface or surfaces have been properly machined to the corrective lens, the projecting member can be removed by breaking a frangible portion or cutting it from the side edge.

Finally, the unitary lens herein is especially well adapted to the formation of protective eyewear, as well as for sport goggles and the like. This is because a plurality of raised portions may be permanently engaged and extend from the first surface of the first lens portion surrounding the raised portions, and the first lens portion is large and panoramic and has thin edges, the unitary structure provides a goggle which is protected from fogging and the like. Further, as noted above, a wafer or layer of polarizing film may be positioned between the lenses, or within the pre formed projecting portions which are later co-molded to the first lens portion, thereby providing polarized eyewear to the user for high glare conditions.

In all modes, both the first lens portion surrounding the engaged projecting portion, and the projecting portion or portions, may be formed of polycarbonate plastic or other optically suitable polymeric or plastic materials, such as a monomer plastic, or a "High Index" plastic.

With respect to the above description, before explaining at least one preferred embodiment of the herein disclosed eyewear invention in detail, it is to be understood that the invention is not limited in its application to the details of construction and to the arrangement of the steps in the following description or illustrated in the drawings. The unitary lens invention herein described is capable of other embodiments and of being practiced and carried out in various ways which will become obvious to those skilled in the art on reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing and carrying out the present disclosed system and eyewear apparatus. It is important, therefore, that the claims be regarded as including such equivalent construction and methodology insofar as they do not depart from the spirit and scope of the present invention.

BRIEF DESCRIPTION OF DRAWING FIGURES

FIG. 12 depicts a mode of the device forming a unitary lens structure which is adapted for engagement in eyeglass frames where the thinner cross section of the first lens portion surrounds the thicker area where the projecting portion is engaged.

FIG. 13 is an overhead view of the device as in FIG. 12 showing the intersection surrounding the perimeter sidewall defining the shape of the oval projecting portion and the first surface of the first lens portion.

FIG. 14 depicts a sectional view of the device of FIGS. 12 and 13 and shows the preferred non linear intersection of the sidewall defining the projecting portion, with the first surface of the first lens portion.

FIGS. 15a-15d depict various preferred shapes to the intersection of the sidewall with the first surface of the first lens portion, to eliminate the linear intersection prone to cracking.

Other aspects of the present invention shall be more readily understood when considered in conjunction with the above noted accompanying drawings, and the following detailed description, neither of which should be considered limiting.

DETAILED DESCRIPTION OF THE PREFERRED EMBODIMENTS OF THE INVENTION

Figure 1:
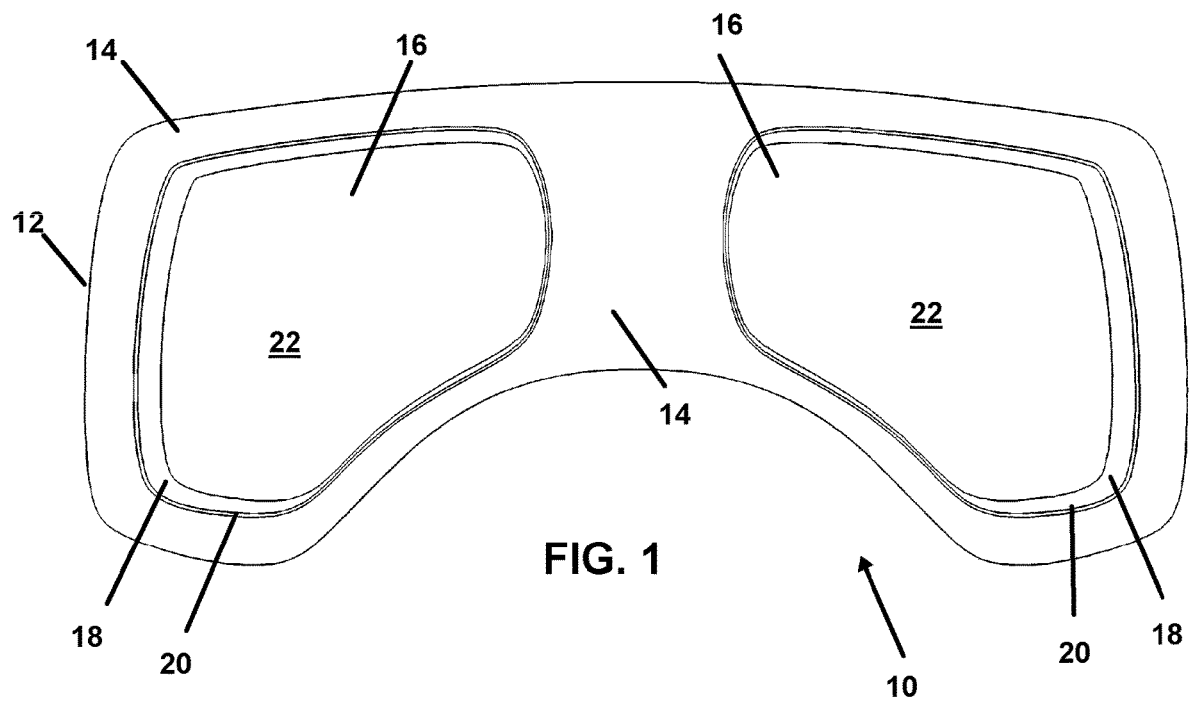
FIG. 1 depicts a view of the first surface of a first lens portion having a plurality of raised portions with shapes defined by a perimeter sidewall, extending away therefrom.

Now referring to drawings of FIGS. 1-19, where similar structures are described with like numerals there is seen in FIG. 1 depicts a view of a mode of the device 10 having a unitary structured lens, formed of a first lens portion 12 having a first surface 14, and having at least one, or as shown preferably a plurality of projecting or projecting portions 16 extending therefrom. The projecting portions 16 have a shape defined by a perimeter formed by a sidewall 18 which extends away from an intersection 20 at a first end of the sidewall 18, with the first surface 14 of the first lens portion 12. The sidewall 18 of each projecting portion 16 extends to a distal end, at an intersection with the edge of a projecting surface 22 formed within the perimeter defined by the sidewall 18. The projecting surface 22, is adapted for formation of an ophthalmic lens to correct the vision of a user or wearer.

A particularly preferred shape of the projecting portions 16 is shown in FIG. 1. As shown, each of the two projecting portions 16 has a respective wider diameter adjacent the two ends of the curved first lens portion 12, and have narrower diameters at their respective ends, adjacent the middle.

This preferred shape allows for portions of the projecting portions 16 to extend closer to the bridge of the nose, while concurrently extending to the temple and well below the nose. This extended rectangular shape, with a curve extending from a nose-side of the projections 16 to a lower edge adjacent both ends of the first lens portion 12, allows for formation of progressive lenses, using the projecting portions 16, and prescriptive eyewear which are highly customized, as the formed progressive lens can be both horizontal from top to bottom, and sideways from nose end to temple end.

Figure 2:
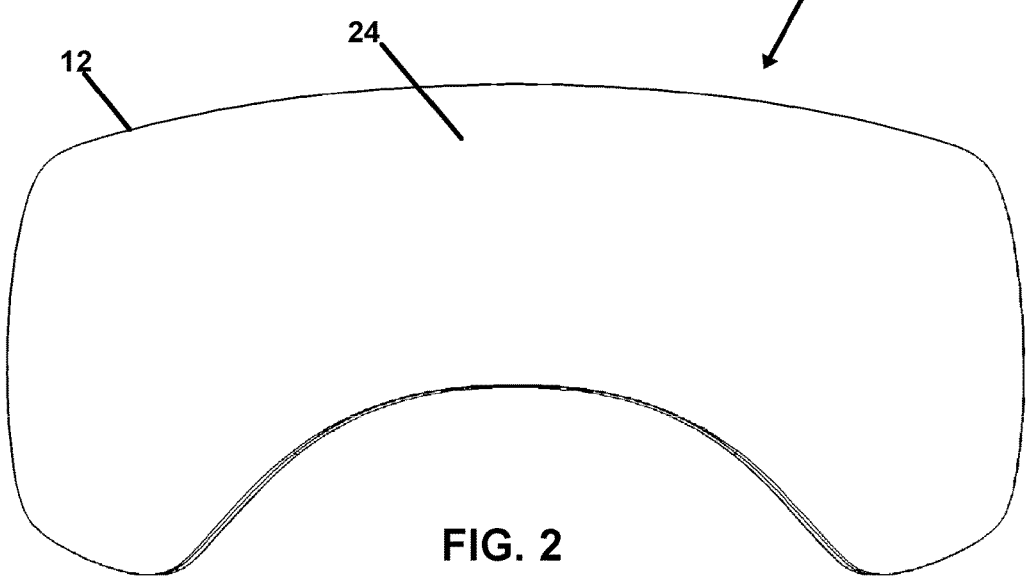
FIG. 2 depicts a view of the opposite side of the first lens portion from FIG. 1 showing the second surface and the shadowless appearance of the second surface provided by the unitary structure herein.

FIG. 2 depicts a view of the opposite side or second side surface of the first lens portion 12 from that shown in FIG. 1. A novel aspect of the disclosed device 10 is that the formed unitary structure of ophthalmic lens formed on the projecting portion 16 projecting from the first side 14 of the first lens portion 12, when viewed from the second surface 24 side, yields a shadowless appearance of the second surface 24 even where a filter material may be inserted as noted below.

Figure 3:
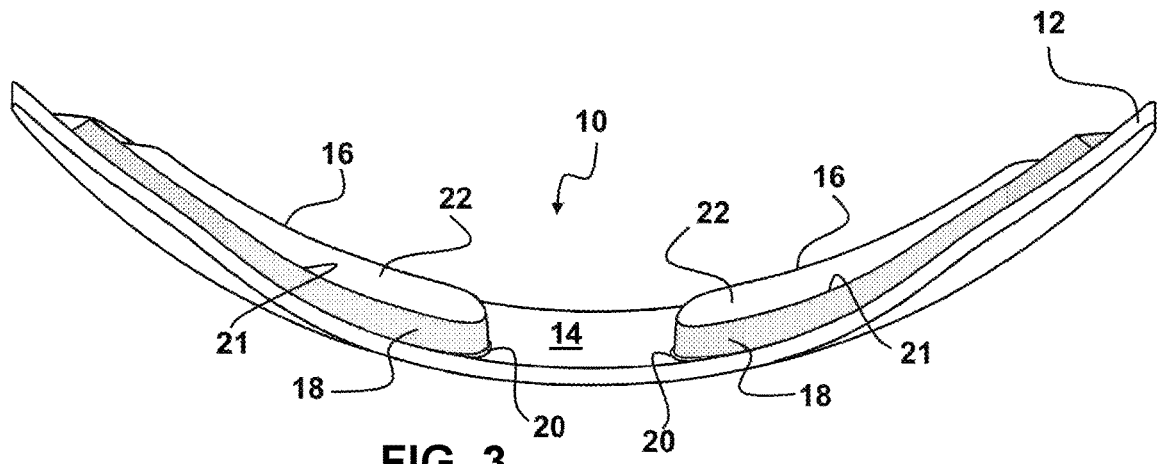
FIG. 3 depicts a perspective view of the view of FIG. 1 showing two projecting portions having a shape defined by a perimeter sidewall extending from the first surface of the first lens portion.

Shown in FIG. 3 is a perspective view of the device 10 shown in FIG. 1. Depicted are a plurality of two projecting portions 16 each having a shape defined by the perimeter of a sidewall 18 extending from an intersection 20 with the first surface 14 of the first lens portion 12. As can be seen the cross sectional thickness of the first lens portion 12 surrounds the formed projecting portions 16 and is significantly thinner. As noted, the projecting portions 16 and first lens portion 12 are formed in a unitary structure, either by a single mold with the projections 16 and lens portion 12, or by co molding formed projecting portions 16 into the mold for the first lens portion 12 which melts and forms the projecting portions 16 into the structure of the first lens portion 12.

Figure 4:
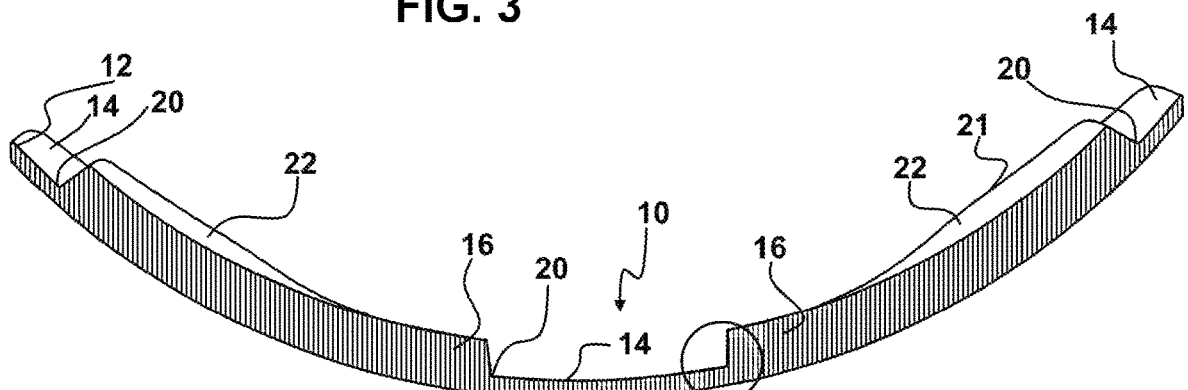
FIG. 4 is a sectional view through FIG. 3 showing the unitary structure formed by the projecting portions and first lens portion and the non linear intersection of the sidewall of the projecting portions with the first surface of the first lens portion.

In the depiction of FIG. 4 is shown a sectional view through the device as in FIGS. 1 and 3 showing the unitary structure of the first lens portion 12 and projecting portions 16. The non linear intersection 20 of the sidewall 18 forming the perimeter and defining the shape of the projecting portions 16 with the first surface 14 of the first lens portion 12 is preferred. As noted above, the non linear intersection 20 of the sidewall 18 with the first surface 14 is most important. By non linear is meant that the line running along the surface of the sidewall 18 running between its communication with the raised surface 22 and the intersection 20, does not intersect the line or planar surface of the first side of the first lens portion.

Instead, at or adjacent to, the intersection 20 of the surface of the sidewall 18 deviates from a planar or straight surface, with an angled portion or curved portion of the surface communicating between the sidewall 18, and the first surface 14. Currently, the angled intersection of FIG. 4c and the curved intersection is in FIG. 4a are particularly preferred as a non linear communication of the sidewall 18 with the first surface 14, however the other noted intersection shapes of FIGS. 4b-4d are also examples of a non linear communication of the sidewall 18 at or adjacent to the first surface 14.

Figure 4A:
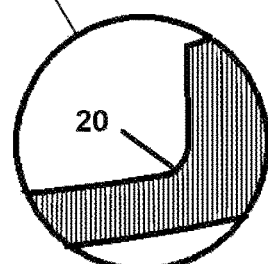
FIG. 4a shows a curved intersection between the sidewall defining the shape of the projecting portion and the first surface of the first lens portion.

FIG. 4a shows a curved surface at the intersection 20 between the sidewall 18 defining the shape of the projecting portion 16 and the first surface 14 of the first lens portion 12.

Figure 4B:
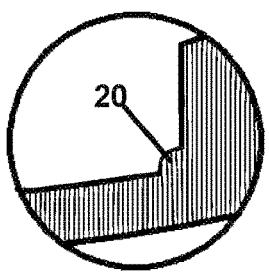
FIG. 4b shows a reverse curved intersection between the sidewall defining the shape of the projecting portion and the first surface of the first lens portion.

FIG. 4b shows a reverse curved shape of the surface of the intersection 20 between the sidewall 18 defining the shape of the projecting portion 16 and the first surface 14 of the first lens portion 12.

Figure 4C:
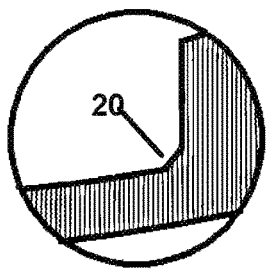
FIG. 4c shows an angled intersection between the sidewall defining the shape of the projecting portion and the first surface of the first lens portion.
Figure 4D:
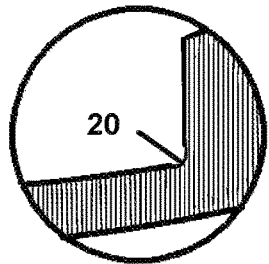
FIG. 4d shows a curved radius relief intersection between the sidewall defining the shape of the projecting portion and the first surface of the first lens portion.

FIG. 4c shows an angled surface of the intersection 20 between the sidewall 18 defining the shape of the projecting portion 16 and the first surface 14 of the first lens portion 12.

FIG. 4d shows a curved relief shaped intersection 20 of the perimeter edge of the sidewall 18, running underneath the first end of the sidewall, 18 and depending into the first surface 14, and running for the perimeter of the projecting portion 1.

Thus, the non linear intersection as defined herein, can be any of a group of non linear intersections, including an intersection formed by a curved surface extending between said first end of said sidewall and said first surface of said first lens portion as in FIGS. 4a and 4b, an intersection formed by an angled surface extending between said first end of said sidewall and said first surface of said first lens portion as in FIG. 4c, and an intersection formed by a recess extending underneath said first end of said first sidewall 18 and depending into the first surface 14 of said first lens portion 12. This formation of a non linear intersection as noted, prevents cracks.

Figure 5:
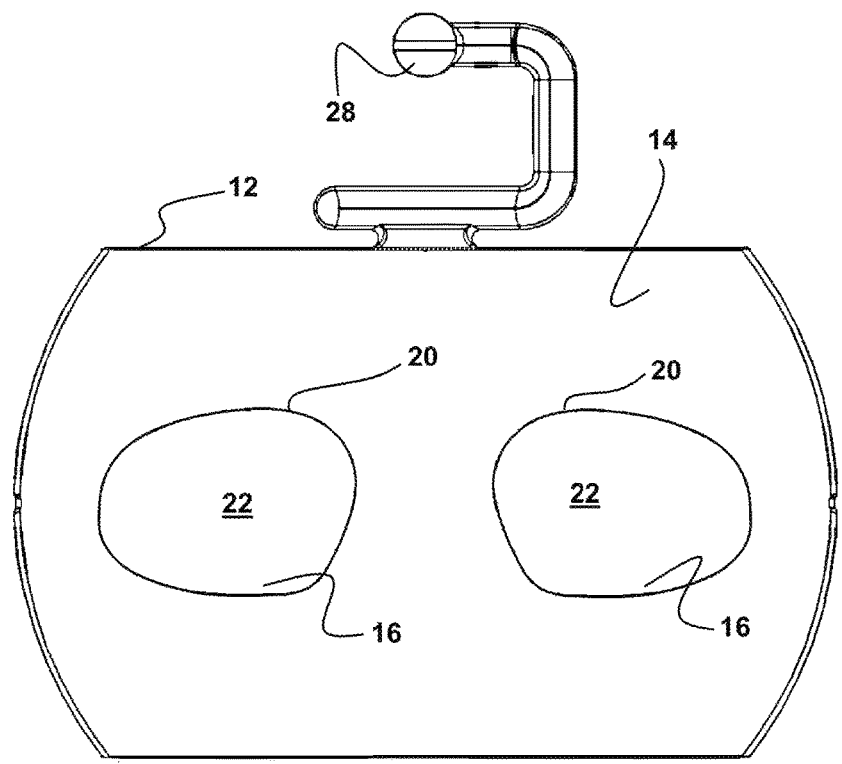
FIG. 5 depicts another mode of the unitary lens structure showing a curved panoramic first lens portion and two circular projecting portions extending from the first surface thereof and showing the centered positioning of a tooling engagement member attached thereto, which may be employed on all versions of the device herein.

As shown in FIG. 5 is depicted another mode of the unitary lens structure device 10 herein. Shown is a curved panoramic first lens portion 12 and two circular projecting portions 16 extending from the first surface 14 of the curved first portion 12 of the formed lens. The perimeter intersection 20 of both sidewalls 18 is shown also and would preferably non linear as noted above. Additionally depicted is a centered tooling engagement member 28 in operative engagement to the first lens portion 12 along a side edge. This tool engagement member may be employed in all modes of the device herein.

Figure 6:
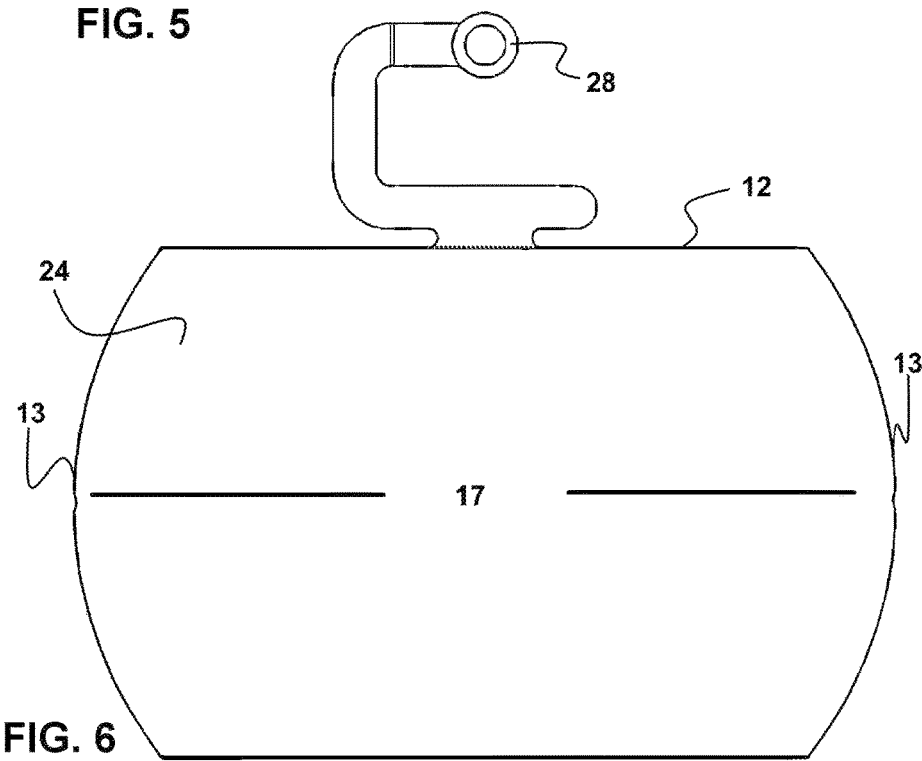
FIG. 6 shows a view of the unitary lens structure of FIG. 5 from the opposite side from FIG. 5 showing the second side surface.

In FIG. 6 is shown an opposite side view of the unitary lens structure of FIG. 5 showing the second side surface 24 and showing the tooling engagement member 28 centered between the two side edges 13 of the first lens portion 12 and extending perpendicular to a horizontal axis running between the two side edges 13.

Figure 7:
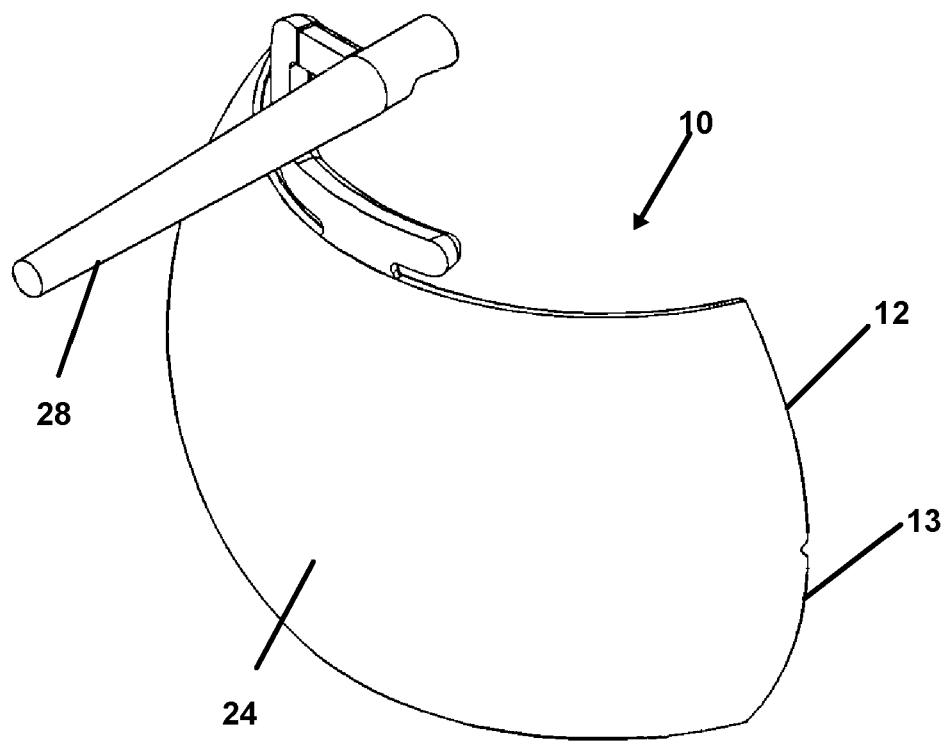
FIG. 7 shows a perspective view of a unitary lens structure such as in FIG. 6, showing the tooling engagement member centered between the two ends of the first lens portion and running perpendicular to an axis running across the first lens portion.

A perspective view of this configuration is shown in FIG. 7. As can bee seen, the tooling engagement member 28 is centered between the two ends 13 of the first lens portion 12 and runs substantially perpendicular to an axis 17 running across the first lens portion 12 between both ends or the temple ends, thereof. As noted this tooling engagement member 28 is adapted for engagement with conventional eyeglass grinding machines, where a goggle lense will not fit or be engageable to form the lenses.

Figure 8:
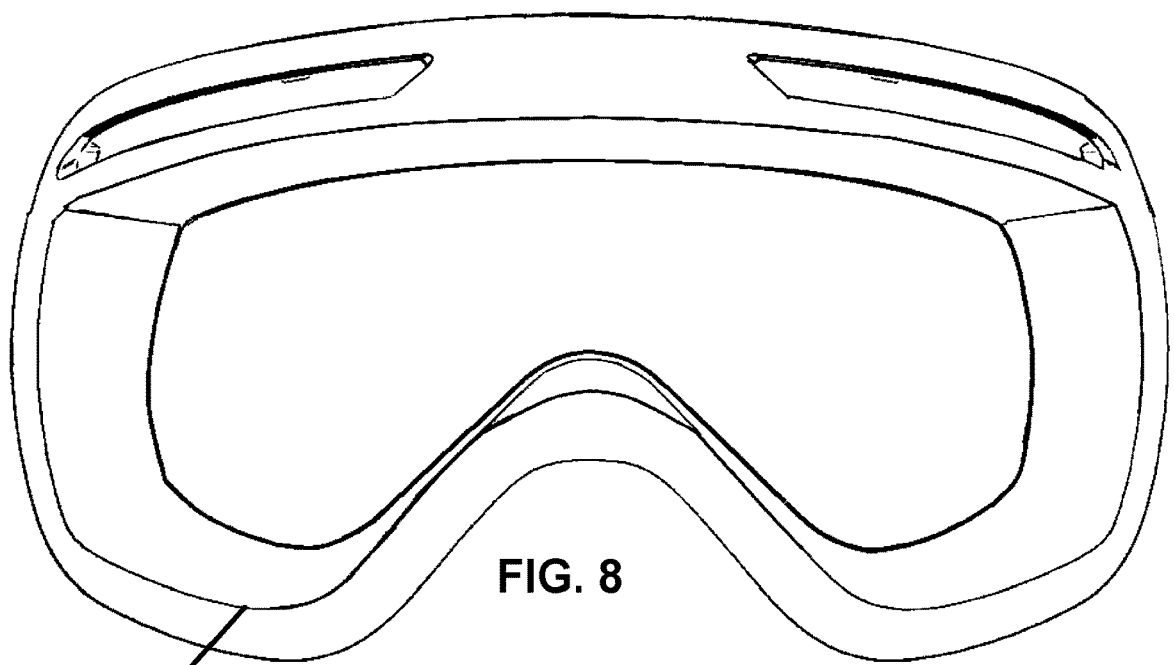
FIG. 8 depicts a sport goggle mode of the device herein.

FIG. 8 depicts a sport or protective goggle mode 33 of the device 10 herein. The configurations shown in FIGS. 9-12 can be engaged with a goggle frame such as in FIG. 8.

Figure 9:
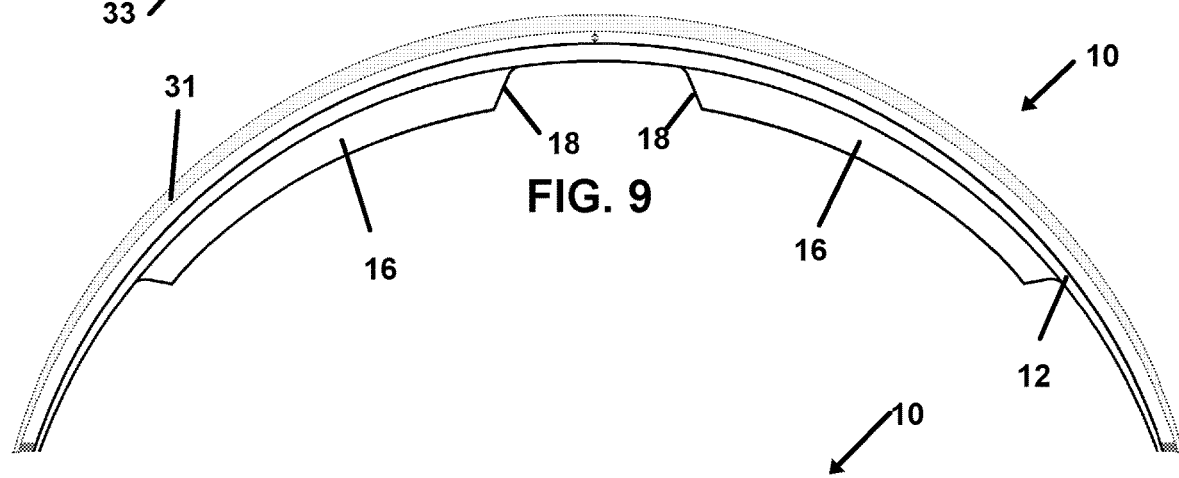
FIG. 9 depicts a first lens portion having two projecting portions thereon and a second lens engaged in a spaced relationship adjacent the second surface of the first lens portion as would be engaged in the goggle of FIG. 8.

In FIG. 9 is shown first lens portion 12 having two projecting portions 16 thereon and having a second lens 31 engaged in a spaced relationship adjacent the second surface 24 of the first lens portion 12 as would be engaged in the goggle of FIG. 8.

Figure 10:
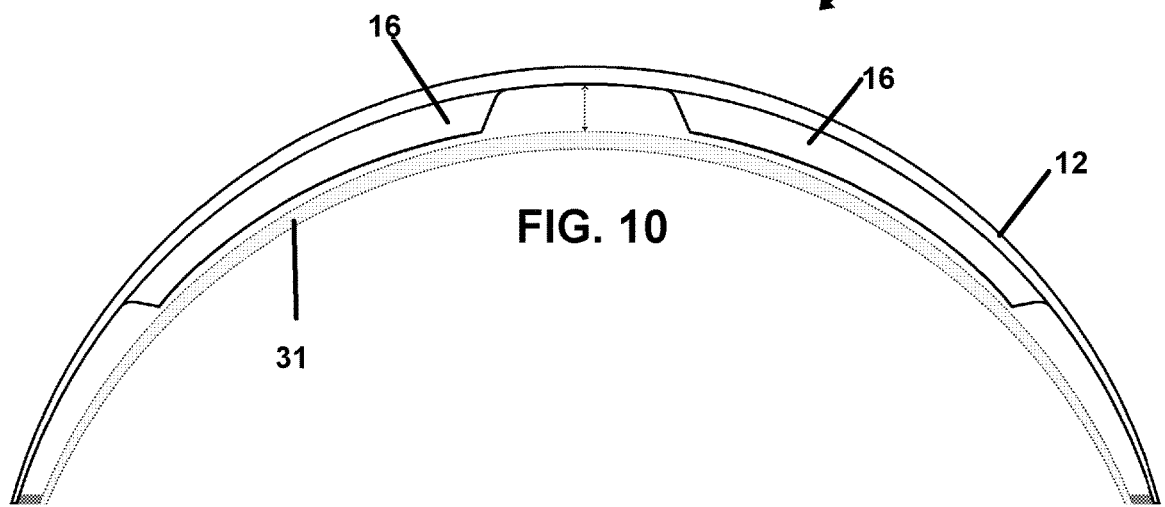
FIG. 10 shows the device in a similar fashion to that of FIG. 9, engageable within the goggle frame of FIG. 8, wherein the second lens forming a cavity is positioned adjacent to the raised lens-machinable surfaces of the projecting portions.

Shown in FIG. 10 is a mode of the device 10 similar in fashion to that of FIG. 9 and engageable within the goggle frame 33 such as that of FIG. 8. In this figure, the second lens 31 forming a cavity is positioned adjacent to the lens-machinable raised surfaces 22 of the projecting portions 16.

Figure 11:
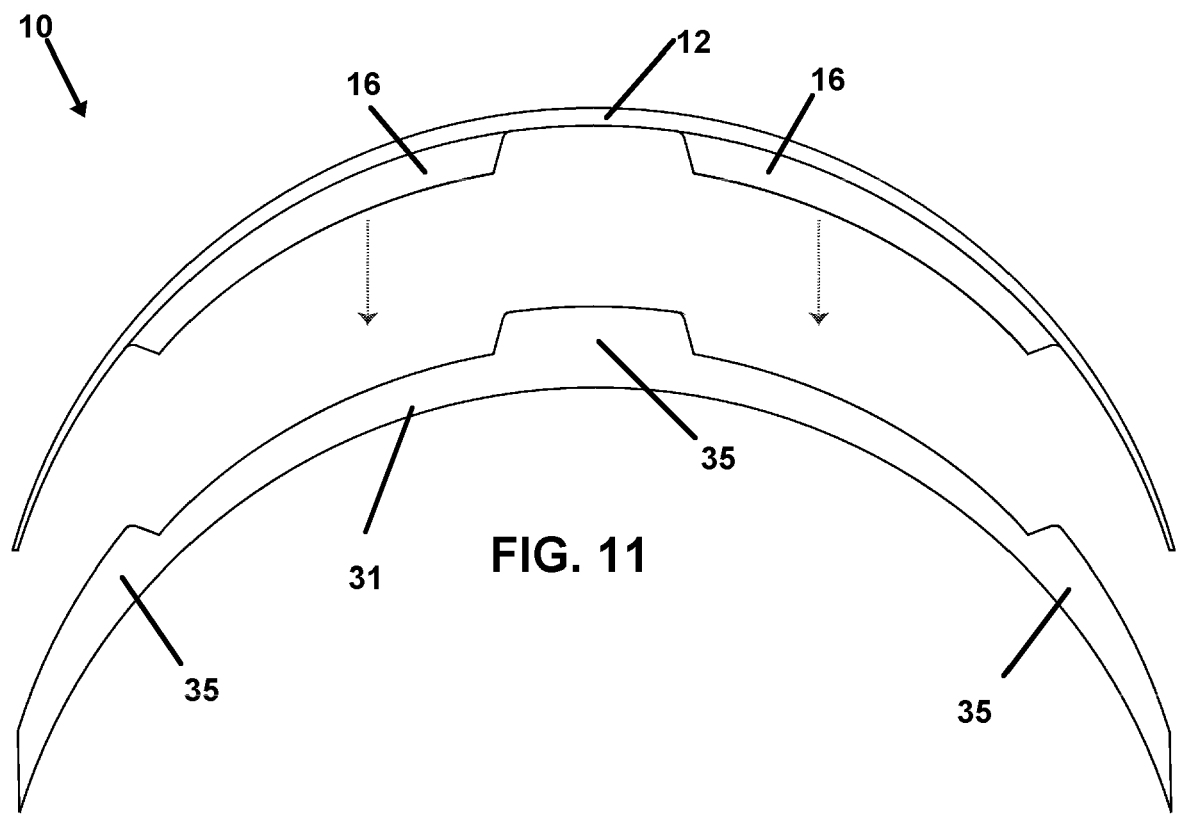
FIG. 11 shows another mode of the device adapted for a goggle to minimize fogging in the same fashion as those of FIGS. 9, 10, and 12, and showing a mating lens having projecting sections adapted to fit adjacent the sidewalls of the formed projecting portions of the first lens.

Another goggle or protective eyewear mode is shown in FIG. 11 and adapted to minimize fogging in the same fashion as those of FIGS. 9, 10, and 12. As depicted, a mating second lens 31 having projecting sections 35 is engageable where the projecting sections 35 are configured to fit adjacent the sidewalls 18 of the formed projecting portions 16 of the first lens 12 and fill the gaps.

FIG. 11 shows another mode of the device adapted for a goggle to minimize fogging in the same fashion as those of FIGS. 9, 10, and 12, and showing a mating lens having projecting sections adapted to fit adjacent the sidewalls of the formed projecting portions of the first lens.

FIG. 12 depicts a mode of the device forming a unitary lens structure formed with a first lens portion 12 and projecting portion 16 as with the other modes herein. This mode of the device is well adapted for engagement in eyeglass frames where the thinner cross section of the first lens portion 12 which surrounds the thicker area where the projecting portion 16 rises will better fit frames.

FIG. 13 is an overhead view of the device as in FIG. 12 showing the perimeter intersection 20 of the sidewall 18 with the first surface 14 of the first lens portion 12. As depicted the sidewall 18 defines an oval projecting portion 16 extending from the first surface 14 of the first lens portion 12.

FIG. 14 depicts a sectional view of the device of FIGS. 12 and 13 and shows the preferred non linear intersection 20 between the sidewall 18 and the first surface 14 of first lens portion 12 as is preferable in all modes of the device herein.

FIGS. 15a-15d depict various non linear shapes to the intersection 20 of the sidewall 18 with the first surface 14 of the first lens portion 12. Such as noted are highly preferred to eliminate a linear intersection prone to cracking.

Figure 16:
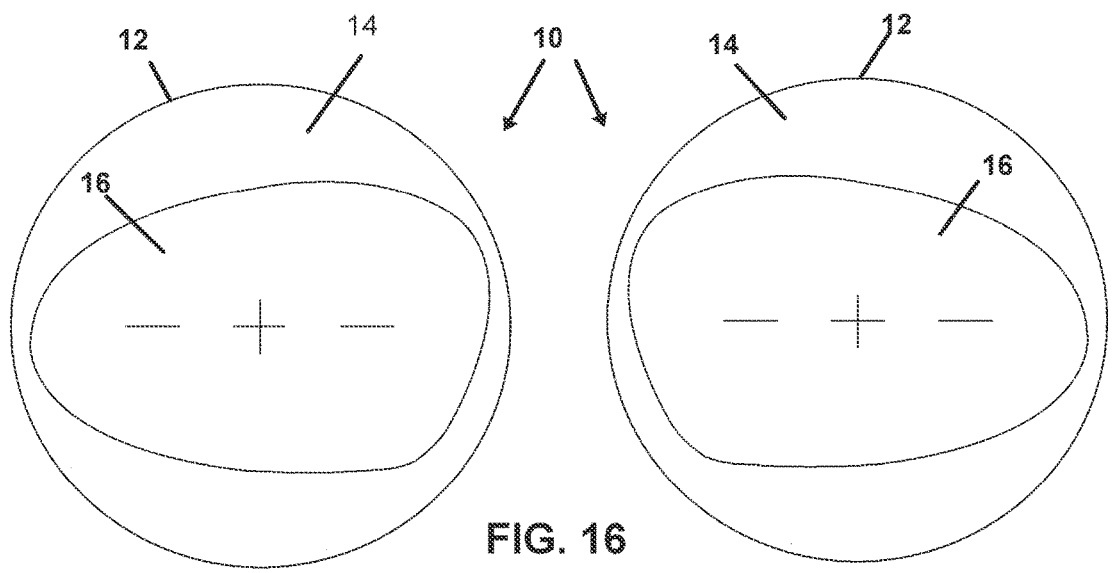
FIG. 16 depicts unitary lenses formed to engage eyeglass frames where the thicker projecting portion is surrounded by the thinner first lens surface to allow engagement to more fashionable eyewear when the user must have thick lenses for sight correction.
Figure 17:
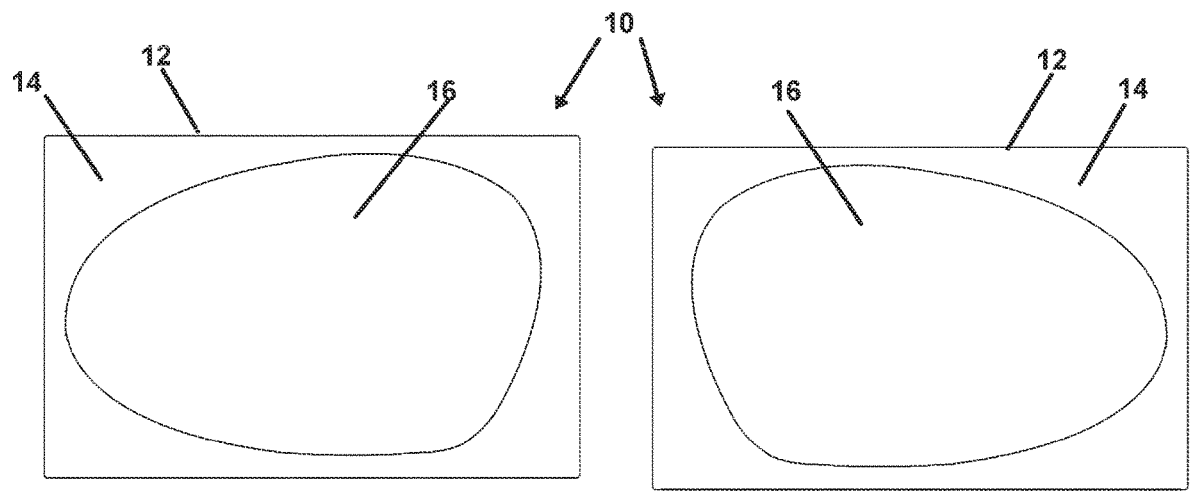
FIG. 17 depicts another mode of the device as in FIG. 16 but with rectangular panoramic first lens portions.
Figure 18:
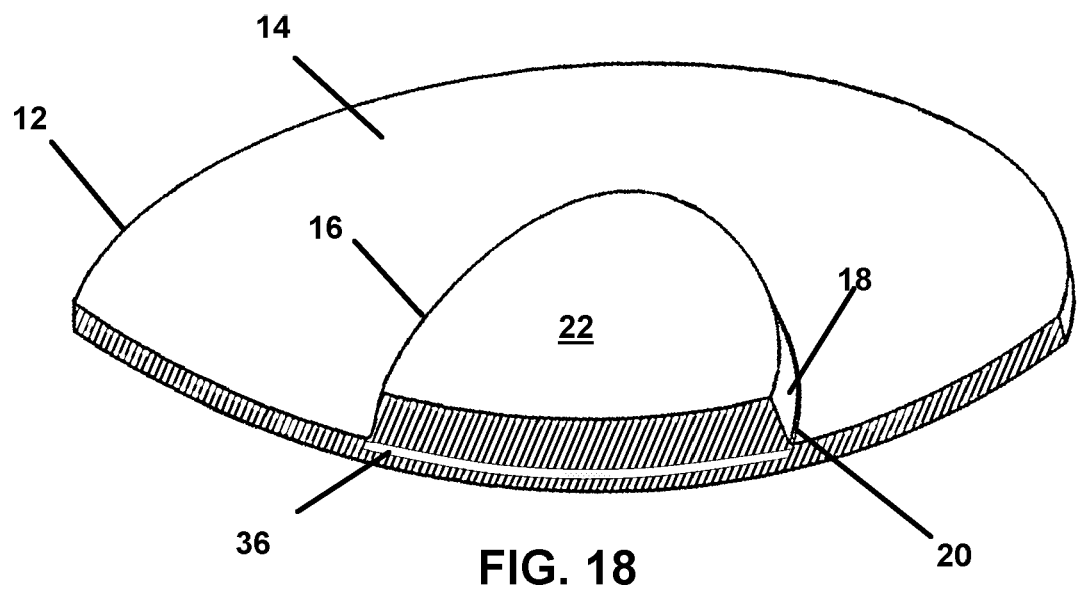
FIG. 18 shows the unitary lens structure herein having a polarizing or other filter engaged between the projecting portion and the first lens portion and which can be included with any form of the unitary lens herein.
Figure 19:
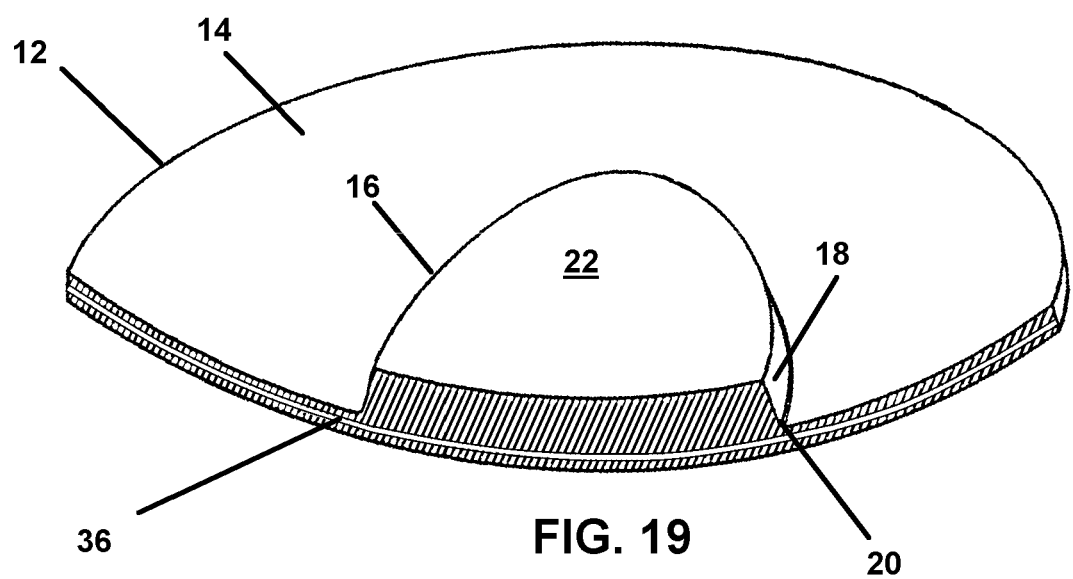
FIG. 19 depicts the unitary lens structure where the polarizing or other filter layer is positioned across the entire first lens component in between the first surface and second surface thereof.

FIG. 16 depicts unitary lense devices 10 formed to engage eyeglass frames where the thicker projecting portion 16 is surrounded by the thinner first lens portion 12 to allow for optical prescriptions requiring thick lenses, but also allow engagement of the formed lens devices 10 to more fashionable eyewear when the user must have such thick lenses for sight correction. In FIG. 17 is shown a similar mode of the device 10 as in FIG. 16, but with rectangular panoramic first lens portions 12.

Where filtered optics are desired or required in the device 10 herein in any mode, such is depicted in FIG. 18 and FIG. 19. In FIG. 18 is shown the unitary lens device 10 which has a polarizing or other filter layer 36 engaged between the projecting portion 16 and the second side 24 of the first lens portion 12. Shown in FIG. 19 the polarizing or other filter layer 36 is positioned across the entire first lens portion 12 in between the first surface 14 and second surface 24 thereof.

While all of the fundamental characteristics and features of the software enabled employee management and matching system herein have been shown and described herein, with reference to particular embodiments thereof, a latitude of modification, various changes and substitutions are intended in the foregoing disclosure and it will be apparent that in some instances, some features or steps in the invention may be employed without a corresponding use of other features or steps without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A corrective lens comprising:
a first lens portion extending in a panoramic curve from a first end thereof to a second end thereof;
a central area of said first lens portion in-between said first end and second end of said first lens portion;
said first lens portion having a first surface having a first curve opposite a second surface having a second curve;
a first projecting portion extending from said first surface of said first lens portion, said first projecting portion having a first sidewall thereof extending to a first side surface thereof;
said first side surface of said first projecting portion being processible to configure said first projecting portion to a first corrective lens; and
said first lens portion configured for an operative engagement with an eyeglass frame or goggle which is positionable to an as-worn position upon a user, to locate the first surface thereof facing the eyes of a user with the first projecting portion aligned with a first eye of the user.

2. The corrective lens of claim 1 additionally comprising:
said first projecting portion extending in a first curve from a first side of said first sidewall thereof within said central area of said first lens portion, to a second side of said first sidewall thereof located adjacent said first end of said first lens portion;
said first side surface of said first projecting portion being processable for curved horizontal vision correction therethrough along said first curve; and
said first side of said first projecting portion processable for vertical vision correction therethrough, between a top of said first sidewall of said first projecting portion and an opposite bottom of said first sidewall of said first projecting portion.

3. The corrective lens of claim 1 additionally comprising:
a second projecting portion extending from said first surface of said first lens portion, said second projecting portion having a second sidewall thereof extending to a second side surface thereof;
said second side surface of said second projecting portion being processible to configure said second projecting portion to a first corrective lens; and
wherein with said first lens portion in said as-worn position upon a user said second projecting portion aligned with a second eye of the user.

4. The corrective lens of claim 2 additionally comprising:
a second projecting portion extending from said first surface of said first lens portion, said second projecting portion having a second sidewall extending to a second side surface thereof;
said second projecting portion extending in a second curve from a first side of said second sidewall thereof within said central area of said first lens portion, to a second side of said second sidewall located adjacent said second end of said first lens portion;
said second side surface of said second projecting portion being processable for curved horizontal vision correction therethrough along said second curve;
said second side surface of said second projecting portion processable for vertical vision correction therethrough, between a top of said second sidewall of said second projecting portion and an opposite bottom of said second sidewall of said first projecting portion; and
with first lens portion in said as-worn position upon a user the second projecting portion is aligned with a second eye of the uses.

5. The corrective lens of claim 4 additionally comprising:
said first sidewall defining a first shape of said first projecting portion, said first shape being substantially rectangular; and
said second sidewall defining a second shape of said second projecting portion, said second shape being substantially rectangular.

6. The corrective lens of claim 4 additionally comprising:
said bottom of said first sidewall having a first curved section therein;
said bottom of said second sidewall having a second curved section therein; and
said first curved section and said second curved section defining an area therebetween for positioning of a nose of the user.

7. The corrective lens of claim 3 additionally comprising:
said first lens portion having a layer of light filtering material.

8. The corrective lens of claim 4 additionally comprising:
said first lens portion having a layer of light filtering material.

9. The corrective lens of claim 3 additionally comprising:
said first sidewall defining a first shape of said first projecting portion;
said first shape being a first extended rectangular shape where said second end of said first projecting portion positioned closest to said first end of said first lens portion and is wider than said first end of said first projecting portion in said central area of said first lens portion;
said second sidewall defining a second shape of said second projecting portion; and
said second shape being a second extended rectangular shape where said second end of said second projecting portion positioned closest to said second end of said first lens portion is wider than said first end of said second projecting portion in said central area of said first lens portion.

10. The corrective lens of claim 4 additionally comprising:
said first sidewall defining a first shape of said first projecting portion;
said first shape being a first extended rectangular shape where said second end of said first projecting portion positioned closest to said first end of said first lens portion and is wider than said first end of said first projecting portion in said central area of said first lens portion;
said second sidewall defining a second shape of said second projecting portion; and
said second shape being a second extended rectangular shape where said second end of said second projecting portion positioned closest to said second end of said first lens portion is wider than said first end of said second projecting portion in said central area of said first lens portion.

11. The corrective lens of claim 6 additionally comprising:
said first sidewall defining a first shape of said first projecting portion;
said first shape being a first extended rectangular shape where said second end of said first projecting portion positioned closest to said first end of said first lens portion and is wider than said first end of said first projecting portion in said central area of said first lens portion;
said second sidewall defining a second shape of said second projecting portion; and
said second shape being a second extended rectangular shape where said second end of said second projecting portion positioned closest to said second end of said first lens portion is wider than said first end of said second projecting portion in said central area of said first lens portion.

12. The corrective lens of claim 7 additionally comprising:
said second surface of said first lens portion having a shadowless appearance.

13. The corrective lens of claim 8 additionally comprising:
said second surface of said first lens portion having a shadowless appearance.

14. The corrective lens of claim 3 additionally comprising:
a second lens extending to a second perimeter edge thereof;
said second lens extending in a secondary curve thereof; and
a gap positioned between said second lens and said second surface of said first lens portion.

15. The corrective lens of claim 4 additionally comprising:
a second lens extending to a second perimeter edge thereof;
said second lens extending in a secondary curve thereof; and
a gap positioned between said second lens and said second surface of said first lens portion.

16. The corrective lens of claim 3 additionally comprising:
a second lens extending to a second perimeter edge thereof;
said second lens extending in a secondary curve thereof;
a gap positioned between said second lens and said second surface of said first lens portion; and
said first projection portion and said second projecting portion positioned within said gap.

17. The corrective lens of claim 4 additionally comprising:
a second lens extending to a second perimeter edge thereof;

said second lens extending in a secondary curve thereof; and a gap positioned between said second lens and said second surface of said first lens portion; and said first projection portion and said second projecting portion positioned within said gap.

* * * * *